(12) United States Patent
DeSha

(10) Patent No.: US 6,441,387 B1
(45) Date of Patent: Aug. 27, 2002

(54) BIOLOGICAL AEROSOL TRIGGER (BAT)

(75) Inventor: Michael S. DeSha, Abingdon, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/343,619

(22) Filed: Jun. 30, 1999

(51) Int. Cl.[7] .......................... G01N 21/85; G01N 21/00
(52) U.S. Cl. .......................... 250/573; 356/338; 356/343
(58) Field of Search .................. 250/573, 574; 356/337, 338, 340, 343, 436, 440, 246

(56) References Cited

U.S. PATENT DOCUMENTS

| | | | | |
|---|---|---|---|---|
| 3,624,835 A | * | 11/1971 | Wyatt | 356/343 |
| 4,006,990 A | * | 2/1977 | Munk | 356/246 |
| 4,320,978 A | * | 3/1982 | Sato | 356/440 |
| 4,907,884 A | * | 3/1990 | Wyatt et al. | 356/343 |
| 4,942,305 A | * | 7/1990 | Sommer | 356/343 |
| 5,905,271 A | * | 5/1999 | Wynn | 250/573 |
| 6,193,936 B1 | * | 2/2001 | Gardner et al. | 422/186 |

* cited by examiner

*Primary Examiner*—Frank G. Font
*Assistant Examiner*—Zandra Smith
(74) *Attorney, Agent, or Firm*—Ulysses John Biffoni; Vincent J. Ranucci

(57) ABSTRACT

An aerosol triggering device with an integrating sphere and direct air flow provides a simple and efficient biological aerosol trigger. A method for detecting biological aerosols using the aerosol triggering device also is disclosed.

19 Claims, 2 Drawing Sheets

BIOLOGICAL AEROSOL TRIGGER (BAT)

Government Interest

The invention described herein may be manufactured, licensed, and used by or for the U.S. Government.

BACKGROUND OF THE INVENTION

1. Field of the Invention

The present invention relates to biological aerosol detection. In particular, the present invention relates to a triggering device for warning of biological aerosol contaminants. Most particularly, the present invention triggers a suite of biological sample collectors with the positive indication of the presence of an aerosol biological contaminant.

2. Brief Description of the Related Art

With the threat of biological aerosol contaminants to military units and civilian communities, several systems have been developed to provide standoff detection of the biological agents. Although some of the systems possess substantial range capabilities, such as up to 100 kilometers, to detect generated biological aerosols, the systems are generally large and consume considerable power. In many circumstances, use of the large systems becomes problematic, such as being used in conjunction with a small mobile force, or in isolated areas. In these situations, smaller point sensors are needed.

Generally, smaller point sensors provide a reduced capability in detecting aerosol agents. One method of increasing the capability of the sensor was to develop an instrument that provided a trigger for a suite biological sample collectors. The triggering method was based on an increase in the concentration of a particular sized particle, however, the method proved in-effective for field operations.

One technology used to determine the presence or absence of biological contaminants includes an instrument called Laser Induced Fluorescence. All biologically based materials are composed of proteinaceous molecules, which auto-fluoresce when exposed to electromagnetic radiation, i.e. light, at an excitation wavelength. The excitation wavelength is any wavelength that couples into the absorption band of the biological compound sample. Once the compound adsorbs the radiation, the radiation is elastically (directly scattered) and inelastically (fluorescence) scattered. The inelastic scatter signature indicates whether the compound is biological in nature.

Previous three point sensors, based on laser induced fluorescence of biological materials, have experienced problems. In one design developed by Lincoln Labs of Concord, Mass., laser beams interact with the biological aerosol in a volume that is imaged onto two detectors with two large concave mirrors. Although the design appears to work well, it is very sensitive to misalignment and internal component contamination. Another design developed by Science and Technology Corporation of Hampton, Va. in conjunction with the Laser Standoff Detection Team of Chemical Biological Center, Aberdeen Proving Ground, Md. takes advantage of natural wind flow through the instrument and does not use mechanical pumps. As an open optical system, this design possesses the disadvantage of allowing solar radiation to enter the system, increasing system noise. Optical baffling may decrease the signal noise, but baffles also disrupt airflow through the system. Other point type triggers have not eliminated the problems of laser beam misalignment and instrument contamination.

Integrating spheres are optical instruments used primarily for optical calibration of detectors and sources. Integrating sphere are described in "A Guide to Integrating Sphere Theory and Applications" published by labsphere® of North Sutton, N.H., the disclosure of which is herein incorporated by reference.

SUMMARY OF THE INVENTION

In view of the foregoing, it is therefore an object of the present invention to eliminate the need to maintain alignment of the laser beam within the aerosol sample volume in relation to the point sensor detector elements.

These and other objects are achieved by the present invention which includes an aerosol triggering device, comprising a conduit forming a passage for an air flow, said conduit including an aerosol intake port and an aerosol exit port, wherein an air flow is capable of passing into said conduit through said aerosol intake port and exiting said conduit through said aerosol exit port; an optical chamber having at least two detectors capable of detecting an increase in the presence of a biological aerosol within an air flow, said optical chamber being in gaseous and optical communication with said conduit, wherein air flow entering said aerosol intake port is capable of entering said optical chamber prior to exiting through said aerosol exit port; a laser beam entrance window attached to said conduit and permitting entry of a laser beam into said conduit and said optical chamber; a laser beam exit window attached to said conduit capable of optical alignment with said laser beam entrance window; and, a laser beam system having a laser beam generation source capable of optically directing a laser beam of a selected frequency into said conduit and said optical chamber, wherein biological aerosol contaminants within an air flow emit elastic and inelastic scattering. The optical chamber comprises an integrating sphere.

The present invention further includes a method for detecting biological aerosols comprising the steps of providing an aerosol triggering device, comprising a conduit forming a passage for an air flow, said conduit including an aerosol intake port and an aerosol exit port, wherein an air flow is capable of passing into said conduit through said aerosol intake port and exiting said conduit through said aerosol exit port, an optical chamber having at least two detectors capable of detecting an increase in the presence of an aerosol within an air flow, said optical chamber being in gaseous and optical communication with said conduit, wherein air flow entering said aerosol intake port is capable of entering said optical chamber prior to exiting through said aerosol exit port, a laser beam entrance window attached to said conduit and permitting entry of a laser beam into said conduit and said optical chamber, a laser beam exit window attached to said conduit capable of optical alignment with said laser beam entrance window, and, a laser beam system having a laser beam generation source capable of optically directing a laser beam of a selected frequency into said conduit and said optical chamber, wherein biological aerosol contaminants within an air flow emit elastic and inelastic scattering; opening the aerosol intake port, wherein an air flow enters the conduit and into the optical chamber; energizing the laser beam system, wherein the laser beam generation source directs a laser beam into the optical chamber, causing an interaction between the laser beam and air flow; and, detecting the resulting interaction between the laser beam and air flow, wherein the presence of biological contaminants is determined.

Other and further advantages of the present invention are set forth in the description and appended claims.

DETAILED DESCRIPTION OF THE PREFERRED EMBODIMENTS

The present invention is a system that is capable of indicating the presence of biological contaminants based on laser induced fluorescence of proteinacious compounds, The problems of alignment at the interface of the laser beam and aerosol are eliminated by providing an integrating sphere for directing the fluorescence and scatter onto the detectors, and contamination of the internal components is mitigated by providing a simple flow path of the aerosol or air flow. The sensitivity of tile system is unaffected by laser beam misalignment within the air flow by using an integrating'sphere to couple the elastic and inelastic scatter onto the detectors. Inner components of the system are protected from contamination by confining the aerosol flow within a transparent tube. Additionally, the present invention eliminates aerosol losses in the system.

Figure 1:
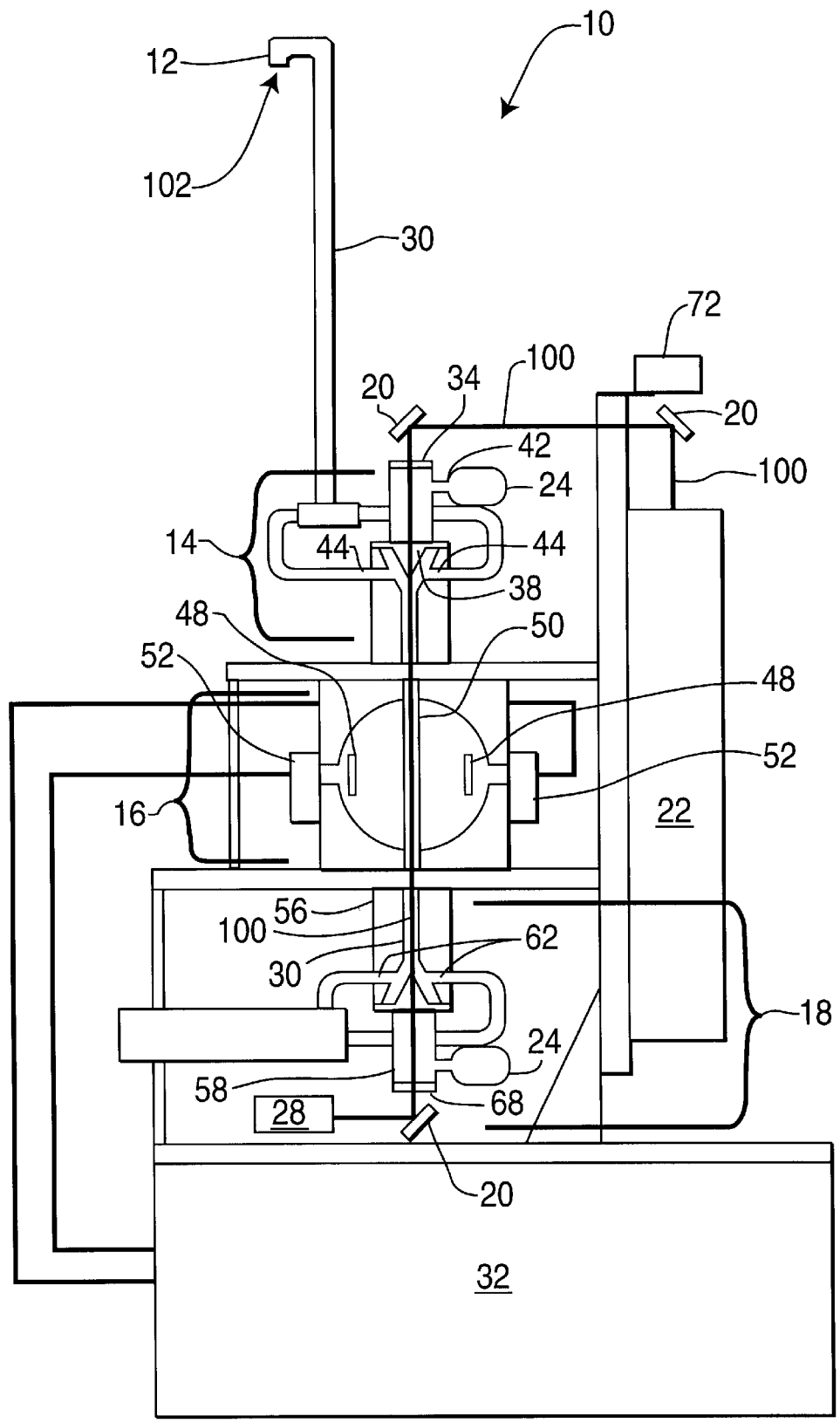
FIG. 1 displays a cut away view of a preferred embodiment of the biological aerosol trigger of the present invention; and, FIG. 2 displays a cut away view of a second preferred embodiment of the biological aerosol trigger of the present invention.

Referring to FIG. 1, the biological aerosol trigger 10 of the present invention is shown. The biological trigger comprises an aerosol intake port 12, aerosol/laser beam interface chamber 14, optical chamber 16, aerosol/laser beam exit chamber 18, laser beam turning mirrors 20, ultraviolet laser 22, HEPA filters 24, laser beam dump 28, and control and signal acquisition electronics 32. Air flow 102, also referred to as an aerosol, within the present invention includes an air sample to be analyzed for biological aerosol contaminants. Generally, air is acquired from an open environment through the aerosol intake port 12. The air flow 102 may contain contaminants in amounts of from about 10 particles per liter or more to be detected.

As seen in FIG. 1, an air flow 102 containing a possible biological aerosol contaminant flows into the biological aerosol trigger 10 through the intake port 12, and passes into a gaseous channel, or conduit 30, that is in communication with the aerosol/laser beam interface chamber 14. The air flow 102 passes into the aerosol/laser beam interface chamber 14, and within the aerosol/laser beam interface chamber 14, the air flow 102 interfaces with a laser beam 100. The aerosol/laser beam interface chamber 14 comprises an upper compartment which contains a laser beam entrance window 34 and clean air inlet 42, and a lower compartment containing one or more aerosol inlets 44, which couples to the upper compartment through a cone shaped nozzle 38. As shown in FIG. 1, after the air flow 102 enters the biological aerosol trigger 10 through the aerosol intake port 12, the air flow 102 passes through at least one aerosol inlet 44 into the lower compartment of the aerosol/laser beam interface chamber 14.

Within the aerosol/laser beam interface chamber 14, the air interacts with the laser beam 100 that originates from the ultraviolet laser 22. The laser beam 100 is directed into the aerosol/laser beam interface chamber 14, by several laser beam turning or steering mirrors 20, through a laser beam entrance window 34. The laser beam 100 enters through the laser beam entrance window 34 into the aerosol/laser beam interface chamber 14, and proceeds through the center axis of the upper compartment of the aerosol/laser beam interface chamber 14, through a cone shaped nozzle 38 and into the lower compartment of the aerosol/laser beam interface chamber 14. Additionally, clean air is drawn through a clean air inlet 42 into the upper compartment of the aerosol/laser beam interface chamber 14, and down through a small hole in the cone shaped nozzle 38 into the lower compartment. This action prohibits aerosols within the air flow 102 from backing into the upper compartment of the aerosol/laser beam interface chamber 14 and fouling the laser beam entrance window 34. The air flow 102 is confined within the aerosol/laser beam interface chamber 14 to eliminate contamination of any optics and detectors of the system, particularly the laser beam entrance window 34 by contaminant aerosols. Once the air flow 102 enters the aerosol/laser beam interface chamber 14, the air flow 102 proceeds along the axis of the aerosol/laser beam interface chamber 14 with the laser beam 100, where the laser beam 100 and air flow 102 enter the optical chamber 16.

Laser beam turning mirrors 20 direct the laser 100 from the ultraviolet laser 22. The ultraviolet laser 22 may be any suitable laser that provides an appropriate wavelength for the detection of biological contaminants, with the type and power of the ultraviolet laser 22 being determinable by those skilled in the art. The intensity and wavelength of the laser beam 100 is controlled by the control and signal acquisition electronics 32, with the laser beam 100 monitored by a laser beam power monitor 72 that provides a feedback to the control and signal acquisition electronics 32 for modulation and refinement of the laser beam 100.

Within the optical chamber 16, the air flow 102 continues to be exposed to the laser beam 100, allowing laser scatter and fluorescence to be detected within the optical chamber 16. The optical chamber 16 of the present invention, shown in FIG. 1, comprises an integrating sphere. The optical chamber 16 includes a direct illumination stop 48, transparent tube 50, optically filtered detectors 52, and control and signal acquisition electronics 32. The laser beam 100 and air flow 102 proceed down the axis of the biological aerosol trigger 10 into the optical chamber 16. Within the optical chamber 16 the elastic and inelastic scatter resulting from the laser beam 100 and aerosol 102 interaction, referred herein as the interaction volume, is viewed by the detectors 52. The signals generated by the detectors 52 are passed on to the control and signal acquisition electronics 32. The detectors 52 may either be mounted at optical ports of the integrating sphere for free space operation, or coupled to the integrating sphere via fiber optics. By using the integrating sphere to optically couple the scattered light onto the detectors 52, the need to align laser beam 100 within the aerosol interaction volume, relative to tile detector elements 52, is eliminated. The integrating sphere is optically unique because all irradiance onto the sphere is uniform and independent of the location of the source. Regardless of where the laser beam 100 is located within the air flow 102, the detectors 52 receive the same signal. As most trigger algorithms depend on the ratio from the resulting elastic and inelastic scatter signals, this aspect of the present invention provides a significant advantage. In systems having signal strength received at the detectors that vary as a function of laser beam location within the interaction volume, a small misalignment may lower sensitivity or even fail to indicate the presence of a biological aerosol.

As the aerosol 102 proceeds through the optical chamber 16, the transparent tube 50 confines the air flow 102. This eliminates contamination of the inner components of the optical chamber 16, and significantly increases the usefulness of the system. A coated transparent tube 50 may be used to filter out some of the laser scatter to reduce detector 52 saturation. Laminar flow is maintained through the transparent tube 50 to allay aerosol deposits on the walls of the transparent tube 50. As the transparent tube 50 becomes too contaminated to use, it may either be replaced or cleaned. In either case, the transparent tube 50 provides a less expensive, easier maintenance, and simpler replacement than other inner components of the biological aerosol trigger 10.

Also shown in FIG. 1, once the aerosol 102 and laser beam 100 exit the optical chamber 16, they pass into the aerosol/laser beam exit chamber 18, which is similar to the aerosol/laser beam interface chamber 14 with the exception of the laser beam 100 and air flow 102 direction. On exiting the optical chamber 16, the air flow 102 passes through the conduit 30 into the aerosol/laser beam exit chamber 18, where it is drawn out of the biological aerosol trigger 10. Like the aerosol/laser beam interface chamber 14, there is a clean air inlet having HEPA filters 24 to eliminate fouling of the laser beam exit window 68. The aerosol 102 proceeds through the upper compartment 56 of the aerosol/laser beam exit chamber 18 and is drawn out of the biological aerosol trigger 10 through aerosol outlets 62 by a vacuum pump 26. A laser beam exit window 68 at the bottom of the aerosol/laser beam exit chamber 18 is attached to the conduit 30 and is in optical alignment with the laser beam entrance window 34. The laser beam 100 proceeds through the upper compartment 56 of the aerosol/laser beam exit chamber 18 through a cone shaped nozzle 66, and into a lower compartment 58. Once the laser beam 100 passes through the aerosol/laser beam exit chamber 18 and out the laser beam exit window 68, it enters the laser beam dump 28. The laser beam dump 28 aids in reducing back-scattering of the laser beam 100 into the biological aerosol trigger 10. The laser beam exit window 68 is kept clean by the barrier of clean air to the air flow 102.

The HEPA filters 24 are in air flow communication with the conduit 30 and work in combination with the vacuum pump. Air flow 102 may be drawn through the biological aerosol trigger 10 by the vacuum pump, after which the air flow 102 passes outside of the biological aerosol trigger 10. Clean air is drawn in through the HEPA filters 24 that purify the incoming outside air into the inside of the aerosol/laser beam interface chamber 14 and aerosol/laser beam exit chamber 18. The clean air in turn prevents contamination of the laser beam entry and exit windows 34 and 68 from exposure to the air flow 102. The laser beam 100 enters the aerosol/laser beam exit chamber 18 through a nozzle that restricts air flow 102 from access into the lower compartment 58. The combination of the clean air and nozzle provides a barrier to the air flow 102 to come in contact with the laser beam exit window 68. This barrier also occurs at the laser beam entry window 34. This reduces the maintenance of the biological aerosol trigger 10, and increases the reliability of the system.

Figure 2:
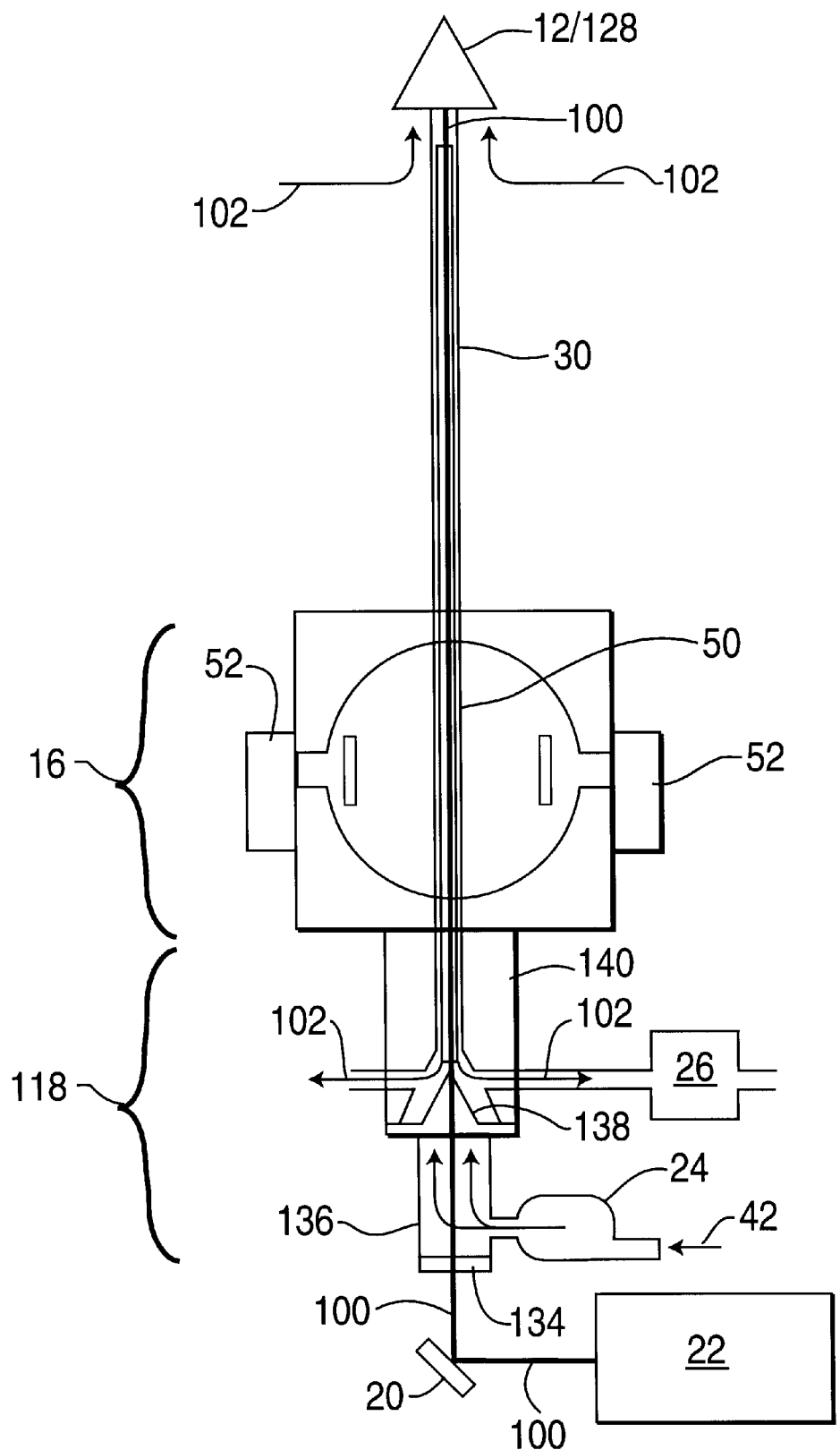

A second embodiment of the present invention is shown in FIG. 2. As seen in FIG. 2, the aerosol/laser beam interface chamber of FIG. 1 was eliminated, and a straight intake tube 12 was incorporated. The laser beam 100 exits at an aerosol exit/laser beam entrance chamber 128. The second embodiment reduces aerosol 102 losses within the biological aerosol trigger 10. The biological aerosol trigger 10 of the second embodiment incorporates within the aerosol exit/laser beam entrance chamber 128 a combination laser beam dump and weather cap. The functioning of the optical chamber 16, ultraviolet laser 22 and related systems, and control and signal acquisition electronics 32 remain the same as the first embodiment of FIG. 1.

The second embodiment of the present invention, incorporating minimal air flow disruptions, provides a simplified air flow 102 for the biological aerosol trigger 10 and reduces noise problems. As found in FIG. 1, an air flow 102 containing a possible biological aerosol contaminant flows into the biological aerosol trigger 10, and interfaces with a laser beam 100, allowing laser scatter and fluorescence to be detected within the optical chamber 16. However, the present invention as seen in FIG. 2 reduces the number of changes in air flow 102 direction, while preserving the interaction between the laser beam 100 and air flow 102.

Air flow 102 is acquired in the biological aerosol trigger 10, shown in FIG. 2, from an open environment through the aerosol intake port 12 that includes a laser beam dump 128, described below. The aerosol intake port 12 may be configured in the form of a weather cap, when desired. Once inside of the biological aerosol trigger 10, the air flow 102 remains confined from the component parts of the biological aerosol trigger 10 to eliminate contamination of any optics and detectors of the system. The air flow 102 enters the biological aerosol trigger 10 through the aerosol intake port 12, passes into a air intake tube or gaseous/optical conduit 30, and continues into the aerosol/laser beam interface chamber 14. In the aerosol/laser beam interface chamber 14, the air flow 102 enters one side of the optical chamber 16, as the laser beam 100 enters the optical chamber 16 from the opposite side. Within the optical chamber 16, the air interacts with the laser beam 100. After reaction with the laser beam 100, the air flow 102 continues to the aerosol exit in the upper chamber 140 of the aerosol exit/laser entrance chamber 118. Above the nozzle 138, the air flow 102 exits the biological aerosol trigger 10, being drawn out through the vacuum pump 26. The laser beam 100 enters the aerosol exit/laser entrance chamber 118, below the air flow 102 exit, at the laser entrance window 134. Additionally, clean air is drawn through a clean air inlet 42, after passing a HEPA filter 24, and into the lower compartment 136 of the aerosol exit/laser entrance chamber 118. The clean air enters between the laser beam entrance window 134 and the air flow 102 exit, passing in the opposite direction of the air flow 102 through the biological aerosol trigger 10. The clean air passes up through a small hole in the cone shaped nozzle 138, and enters the upper compartment 140, thereby stopping the air flow 102 from entering the cone shaped nozzle 138. This action prohibits aerosols within the air flow 102 from entering into the lower compartment 136 and fouling the laser beam entrance window 134. The laser beam 100, originating from the ultraviolet laser 22, is directed into the optical chamber 16 by laser beam turning or steering mirrors 20. On reflection from the steering mirrors 20, the laser beam 100 passes through a laser beam entrance window 134, conduit 30, and into the optical chamber 16. Once the laser beam 100 exits the optical chamber 16, it passes through the conduit 30 and into the beam dump 128.

In either embodiment, the transparent tube 50 provides a less expensive, easier maintenance, and simpler replacement than other inner components of the biological aerosol trigger 10. The optical coupling scheme provided by the integrating sphere provides minimizes the importance of beam location and minimizes the required number of optical interface designs. By incorporating an integrating sphere, having an inner surface of a Lambertian reflector, radiation falling on the surface is diffusely reflected such that the radiance is not a function of angle and is given by:

$$I_s = \rho I / \pi, \quad (I)$$

where $\rho$ is the surface reflectance and $I$ is the irradiance on the surface. The unique trait of an integrating sphere is that the irradiance at the sphere surface is uniform and indepen dent of the location of the source. With the detector placed on the sphere then the radiance on the detector is:

$$d\phi = [\rho\phi_s/(1-\rho 4\pi R^2)]dA \quad \text{(II)}$$

where $\phi_s$ is the source radiance, R is the sphere radius and dA is the area of the detector. The entrance and exit ports provide a modified equation of:

$$d\phi = [\rho\phi_s/(1-\rho)(1-f)4\pi R^2]dA \quad \text{(III)}$$

where $$f = (A_i + A_e)/4\pi R^2 \quad \text{(IV)}$$

and $A_i$ and $A_e$ are the areas of the entrance and exit ports respectively. As seen from equation (III), the radiance at the detector is not a function of source location or proximity. The optical efficiency of the sphere is only few percent, but with a high power laser and a large aerosol sampling volume, the low optical efficiency may be eliminated. Additionally, when using the integrating sphere, the source cannot directly illuminate the detector and all ports must be small compared to the surface of the integrating sphere.

Contamination is maintained at a minimum by limiting the flow to the center of the integrating sphere 46 through the tube 50. The tube 50 comprises transparency parameters at the scatter and fluorescence wavelengths, such as a fused silica tube 50 having a transparency of from about 200 nanometers into the near infrared. Other tubes 50 of the present invention, include for example, a pyrex or transparent Teflon® tube. The laser wavelength used for the laser induced fluorescence technique of the present invention is 266 nanometers (the fourth harmonic of a Neodimium:Yittrium Aluminum Garnet (Nd:YAG) laser), although other wavelengths well known to those skilled in the art may be used to excite various constituents of biological aerosols. The tube 50 is kept clean by maintaining a laminar flow through the tube 50. This keeps contamination to a minimum and allows easy tube replacement when it becomes contaminated. A design that permits easy replacement of the tube includes, for example, an insertion locking mechanism.

EXAMPLE 1

A biological aerosol trigger is used against low concentrations of biological simulants that are disseminated wet or dry. Algorithm parameters are adjusted for eliminating signal noise. Air flow is drawn into the system, which passes to the optical chamber. Signal noise interfered with parts of the test. Once biological contaminants are detected in the air flow, the system triggers a suite of detectors to identify the biological contaminant, with some false triggering events from system noise.

EXAMPLE 2

System tests using the system of the first embodiment indicated that the biological aerosol trigger breadboard improved the performance of the system. The flow tests were run using kaolin dusts and egg albumin and the data indicated a strong fluorescence for the egg albumin and negligible fluorescence with kaolin dust. The trials were conducted using a high concentration of dry aerosols. On disassembly after the trials, the instrument had an accumulation of dust in the lower part of the aerosol/optical interface chamber where the air flow funnels into the Pyrex tube. This was caused by turbulence where the air flow was constricted. Data acquisition and power equipment was mounted in rack beneath the system. The aerosol/optical interface chambers provided adequate protection to keep the optics clean. The laser windows on both the top and bottom were free of dust even after four weeks of trials in desert conditions.

EXAMPLE 3

A system test of the biological aerosol trigger of the second embodiment shows reduced dust accumulation at the completion of the testing. Performance problems of the biological aerosol trigger breadboard was attributed to an interrupted flow through the system causing a reduced signal level in the system. The second embodiment of the biological aerosol trigger reduces aerosol deposition through a straight-line flow, preventing particle losses in the system due to accumulation at bends in the flow path.

It should be understood that the foregoing summary, detailed description, examples and drawings of the invention are not intended to be limiting, but are only exemplary of the inventive features which are defined in the claims.

What is claimed is:

1. An aerosol triggering device, comprising:
   a conduit forming a passage for an air flow, said conduit including an aerosol intake port comprising a weather cap and an aerosol exit port, wherein said air flow is passed into said conduit through said weather cap and exits said conduit through said aerosol exit port;
   an optical chamber having at least two detectors for detecting an increase in the presence of an aerosol within said air flow, said optical chamber being in gaseous and optical communication with said conduit, wherein air flow entering said weather cap is capable of entering said optical chamber prior to exiting through said aerosol exit port;
   a laser beam entrance window attached to said conduit and permitting entry of a laser beam into said conduit and said optical chamber;
   a laser beam exit window attached to said conduit and in optical alignment with said laser beam entrance window; and,
   a laser beam system having a laser beam generation source directing a laser beam of a selected frequency into said conduit and said optical chamber, wherein biological aerosol contaminants within said air flow emit elastic and inelastic scattering.

2. The device of claim 1, wherein said air flow and said laser beam travel in opposite directions.

3. The device of claim 1, wherein said aerosol intake port further includes a laser beam dump.

4. The device of claim 1, wherein said optical chamber comprises an integrating sphere.

5. The device of claim 4, wherein said optical chamber further includes a transparent tube.

6. The device of claim 4, wherein said integrating sphere has an internal diameter of from about 2 inches to about 6 inches.

7. The device of claim 4, wherein said integrating sphere has an internal diameter of from about 3.5 inches to about 4.5 inches.

8. The device of claim 1, wherein said air flow passes through said device in a direct path.

9. The device of claim 1, further comprising a clean air inlet proximate to said laser beam entrance window, wherein said clean air inhibits said air flow from contacting said laser beam entrance window.

10. The device of claim 1, further comprising at least one turning mirror for directing the laser beam into said conduit and said optical chamber.

11. The device if claim 1, wherein said optical chamber includes two or more detectors.

12. The device of claim 1, further comprising an intake pump connected to said conduit to draw said air flow into said aerosol intake port.

13. A method for detecting biological aerosols comprising the steps of:
   (a) providing an aerosol triggering device, said device comprising a conduit forming a passage for an air flow, said conduit including an aerosol intake port comprising a weather cap and an aerosol exit port, wherein said air flow passes into said conduit through said weather cap and exits said conduit through said Aerosol exit port, an optical chamber having at least two detectors capable of detecting an increase in the presence of an aerosol within said air flow, said optical chamber being in gaseous and optical communication with said conduit, wherein air flow entering said weather cap enters said optical chamber prior to exiting through said aerosol exit port, a laser beam entrance window attached to said conduit and permitting entry of a laser beam into said conduit and said optical chamber, a laser beam exit window attached to said conduit in optical alignment with said laser beam entrance window, and, a laser beam system having a laser beam generation source directing a laser beam of a selected frequency into said conduit and said optical chamber, wherein biological aerosol contaminants within said air flow emit elastic and inelastic scattering;
   (b) opening said aerosol intake port, wherein said air flow enters the conduit and flows into said optical chamber;
   (c) energizing said laser beam system, wherein said laser beam generation source directs said laser beam into said optical chamber, causing an interaction between said laser beam and said air flow; and,
   (d) detecting the resulting interaction between said laser beam and said air flow, wherein the presence of biological contaminants is determined.

14. The method of claim 13, wherein said optical chamber comprises an integrating sphere.

15. The method of claim 13, wherein said optical chamber further comprises a transparent tube.

16. The method of claim 13, wherein said air flow through said conduit and said laser beam travel in opposite directions.

17. The method of claim 13, further comprising the steps of:
   providing an intake pump connected to said conduit, wherein said intake pump is activated to draw said air flow into said aerosol intake port.

18. The method of 13, further comprising the step of:
   varying the frequency of said laser beam over a range of settings to cause elastic and inelastic scattering in biological contaminants.

19. The method of claim 13, further comprising the step of:
   providing a clean air inlet proximate to said laser beam entrance window and forcing clean air into said clean air inlet, wherein said clean air inhibits said air flow from contacting said laser beam entrance window.

* * * * *